(12) United States Patent
Serpelloni

(10) Patent No.: US 7,943,171 B2
(45) Date of Patent: May 17, 2011

(54) USE OF BRANCHED MALTO-DEXTRINS AS GRANULATION BINDERS

(75) Inventor: Michel Serpelloni, Beuvry les Bethune (FR)

(73) Assignee: Roquette Freres, Lestrem (FR)

( * ) Notice: Subject to any disclaimer, the term of this patent is extended or adjusted under 35 U.S.C. 154(b) by 574 days.

(21) Appl. No.: 10/534,038

(22) PCT Filed: Oct. 24, 2003

(86) PCT No.: PCT/FR03/03156
§ 371 (c)(1),
(2), (4) Date: May 6, 2005

(87) PCT Pub. No.: WO2004/043166
PCT Pub. Date: May 27, 2004

(65) Prior Publication Data
US 2006/0112956 A1    Jun. 1, 2006

(30) Foreign Application Priority Data

Nov. 6, 2002  (FR) ..................... 02 13868

(51) Int. Cl.
*A61K 9/20* (2006.01)
*C08B 30/00* (2006.01)
*A61K 9/26* (2006.01)

(52) U.S. Cl. .................... 424/464; 127/34; 424/470

(58) Field of Classification Search .............. 424/464; 127/34
See application file for complete search history.

(56) References Cited

U.S. PATENT DOCUMENTS

| | | | |
|---|---|---|---|
| 3,974,032 A | 8/1976 | Harjes et al. | |
| 5,080,908 A * | 1/1992 | Ono et al. | 424/499 |
| 5,204,115 A * | 4/1993 | Olinger et al. | 424/470 |
| 5,458,892 A | 10/1995 | Broderick et al. | |
| 5,582,351 A | 12/1996 | Tsau | |
| 5,612,202 A | 3/1997 | Brumm | |
| 5,886,168 A | 3/1999 | Brumm | |
| 6,348,264 B1 | 2/2002 | Tripodi et al. | |
| 6,630,586 B1 | 10/2003 | Fouache et al. | |
| 2002/0146487 A1 | 10/2002 | Hoshii et al. | |

FOREIGN PATENT DOCUMENTS

| | | |
|---|---|---|
| CA | 2057530 | 6/1992 |
| EP | 1 006 128 | 6/2000 |
| EP | 1153960 | 10/2007 |
| JP | 57134414 | 8/1982 |
| JP | 01063349 | 3/1989 |
| JP | 4287650 | 10/1992 |
| JP | 6-503080 | 4/1994 |
| JP | 08157356 | 6/1996 |
| JP | 2000-37169 | 2/2000 |
| JP | 20000037169 | 2/2000 |
| JP | 2000069939 | 3/2000 |
| JP | 2000-169502 | 6/2000 |
| JP | 2002012560 | 1/2002 |
| WO | 92/10168 | 6/1992 |

OTHER PUBLICATIONS

Velasco et al., "Flow Studies on Maltodextrins as Directly Compressible Vehicles", Drug Development and Industrial Pharmacy, 21 (10), 1995, pp. 1235-1243.
Englyst et al., "Digestions of polysaccharides of potato in the small intestine of man[1-3]", American Journal of Clinical Nutrition, 1987, 45, pp. 423-431.
Japanese Office Action dated Mar. 2, 2010 from JP2004551078.

* cited by examiner

Primary Examiner — Humera N Sheikh
Assistant Examiner — Aradhana Sasan
(74) Attorney, Agent, or Firm — Young & Thompson

(57) ABSTRACT

A method for preparing granules of active substances containing food fibers which consists in granulating the active substances mixed with branched malto-dextrins having between 15 and 35% of 1-6 glucoside bonds, a reducing sugar content less than 20%, a polymolecularity index less than 5 and a number average molecular weight Mn equal or less than 4500 g/mol, the branched malto-dextrins constituting between 3 and 13 wt. % of the mixture to be granulated.

21 Claims, No Drawings

USE OF BRANCHED MALTO-DEXTRINS AS GRANULATION BINDERS

FIELD OF THE INVENTION

The present invention relates to the preparation of granules of active substances containing dietary fiber.

More particularly, the invention relates to a method for preparing granules of active substances containing dietary fiber, which consists in granulating a mixture of said active substances and branched maltodextrins, said branched maltodextrins contents is of between 3 and 13% by weight of the mixture to be granulated. It is also directed toward the use of these branched maltodextrins as active substance granulation binders.

In the context of the present invention, the term "branched maltodextrins" refers to the maltodextrins described in patent application EP 1 006 128, of which the applicant is the proprietor.

These branched maltodextrins have between 15 and 35% of 1-6 glucoside linkages, a reducing sugar content of less than 20%, a polymolecularity index of less than 5 and a number-average molecular mass Mn at most equal to 4500 g/mol.

In addition, the term "active substances" when used herein refers to compounds having dietary and/or pharmaceutical advantages, for instance compounds of the starch or starch derivative type (such as compounds that are generated by acid or enzymatic hydrolysis of starch or compounds that result from the hydrogenation of said starch hydrolysates), or sugars, but also compounds of the strong sweetener type, enzymes, vitamins or pharmaceutical active principles, taken alone or in combination, which exhibit little or no particular capacity for granulation.

Substances such as proteins, in particular soybean proteins, are not selected here since they naturally exhibit coagulation properties that are conventionally taken advantage of in order to granulate them.

BACKGROUND OF THE INVENTION

In the food industry, these active substances may be more particularly polysaccharides or oligosaccharides of the dextrin, maltodextrin, polydextrose or fructo-oligosaccharide type, but also polyols, for instance sorbitol, xylitol, mannitol, lactitol, maltitol, erythritol and isomalt.

It is known practice to use these active substances as such, and also as fillers for other active substances such as strong sweeteners, prepared by chemical synthesis, of the saccharin, aspartame, acesulfame K, cyclamate, stevioside, sucralose, neotame or alitame type.

In the pharmaceutical industry, it may be desirable to use these fillers in combination with, for example, pharmaceutical active principles such as antipyretic analgesics, in particular aspirin and its derivatives, paraminophenol derivatives (such as paracetamol) or pyrazolone derivatives.

Granulation procedures are often used to take full advantage of the powdered form of these active substances or these mixtures of active substances since it is often desirable to increase their particle size for technical and economic purposes.

The two main reasons for this new formulation are:
firstly essentially commercial, given that a granule provides a better appearance and is easier for the user to handle,
secondly strictly technical, because a granule slots more readily into a rational production process, in terms of being more readily conveyed, of better flow, of lack of formation of dust, of better homogeneity in a mixture with other substances, etc.

However, it is extremely rare to be able to risk direct tableting of an active substance or a mixture of active substances, especially if they are effective at very low doses.

It is therefore necessary to formulate these compounds with excipients such as adjuvants (also called granulation binders) in order to confer on the final tablet both mechanical and functional qualities.

Two techniques are normally used to obtain a granule: the wet granulation technique and the dry granulation technique.

In the case of the wet granulation technique, the product to be granulated, that is either naturally wet because of its upstream production procedure, or artificially wetted with a solvent (water or organic solvent), is in a pasty form at the time of granulation.

Two methods are conventionally used for wet granulation: mechanical methods and physical methods.

The mechanical methods consist of grinding, rotor granulation or extrusion methods, well known to those skilled in the art.

Physical granulation methods that use more natural (and thus less aggressive) product granulation technology, by granulating the product either on itself or on an initiator, are however preferred.

The granulation generators per se are centrifugal force, centripetal force or universal gravity, combined with a granulation binder, conventionally consisting of water, of a solution of the product to be granulated, of alcohols or of a glaze, etc.

The product to be granulated is therefore moved around in a tank, for example by means of a pulsed airflow, or on a spherical disk or with a blade rotor (depending on the product and the effect to be obtained).

It continually receives a spray of granulation binders in liquid form to ensure agglomeration.

Thus this method makes it possible to prepare a homogeneous mixture by direct contact between the product to be granulated and the granulation binder. Intimate mixing of the two components is then facilitated.

A horizontal rotary knife can subsequently break up the clods of large agglomerates.

In this method, which is by far the one most preferred by those skilled in the art, it is however necessary for the granulation binder, once dissolved, to have a suitable viscosity, i.e.:
a sufficiently low viscosity to allow the solution containing the granulation binder to be readily pumped, in order to prevent clogging problems at the outlet of the injection nozzles, so as to promote the formation of fine droplets and to provide an even distribution thereof in the granulation tank,
a sufficiently high viscosity to allow the compound to play its role of granulation binder.

The dry granulation technique consists of an operation referred to as "compacting" of the powder to be granulated, thus allowing such procedure to be carried out in simple turbines, or compacters, or in reactors under vacuum.

Use is made of methods of the "sintering" type, which bring about superficial fusion of the particles in contact, thus resulting in granulation by agglomeration.

Use is also made of techniques referred to as "agglomeration by hybridization", which consist in combining only mechanically two distinct particles of different size, in general in a ratio of 1 to 10, in such a way that the small particles either become embedded discontinuously at the surface of the large particle or constitute a continuous film encompassing the entire sphere.

This technology is preferred when granules of thermosensitive active principles must be prepared, since it is known that this method generates only minimal heating, while at the same time promoting mechano-chemical reactions that make it possible to provide good cohesion of the granules.

The granulation binders, depending on their initial particle size, can play this role of large particles that make it possible to attach active substances conventionally having a finer particle size.

Direct association between particles of substances to be granulated and of granulation binders is then promoted.

The drawback of the dry granulation technique is that the subsequent sizing step generates a considerable production of fines.

The wet granulation technique has the advantage of producing no fines or, if it does produce them, doing so in smaller proportions.

However, the choice of using one or the other approach depends especially on the nature of the active substance to be granulated and, most particularly, on its behavior during the granulation operations.

Subsequently, the definitions of the granulation approach and of the granulation binder for granulating said active substance make it possible to adapt the physical and mechanical qualities of the granule obtained, i.e. its mean diameter, its density, its flow capacity, its residual water content and its friability.

Initial studies were interested in the granulation binder qualities that some active substances might themselves have, and thus do not require the addition of exogenous granulation binders that might alter the quality of said active substance to be granulated (such as the glazes or alcohols mentioned above).

Granulation of the active substance is carried out using a diluted solution of this same active substance as a granulation binder.

For example, Velasco et al., in Drug Development and Industrial Pharmacy, 21 (10), 1235-1243, 1995, described the flow properties of maltodextrin powders that could be used as a direct tabletting vector.

According to them, the flow parameter of the starting powder is in fact of critical importance for its formulation.

Some maltodextrins, as long as they have satisfactory flow properties, can thus be advantageously used for granulating other compounds, such as active principles of pharmaceutical interest.

Velasco et al. have measured the bulk density, compressibility, dynamic angle of repose and especially flow capacity parameters of four maltodextrin powders available from the company Grain Processing Corp.

Velasco et al. have especially shown that these maltodextrins have completely different flow capacities, depending on the "friction index" parameter of the powder of the maltodextrins under consideration.

Some maltodextrins are entirely satisfactory, whereas others, such as Maltrin® M 150, do not even pass through the orifice of the device for measuring the flow capacity.

This great behavioral heterogeneity of said maltodextrins does not therefore promote their unconditional use in granulation, and therefore only partially facilitates their selection as granulation binders.

The other active substances, such as sugars, polyols, strong sweeteners or enzymes, do not have any particular capacities for granulation.

Xylitol or mannitol crystals for example show no capacity for direct tabletting, neither do strong sweeteners such as aspartame.

For these particular active substances, an exogenous granulation binder is therefore essential for their formulation as granules.

U.S. Pat. No. 5,583,351 describes a method for preparing a dense product based on aspartame in powdered form, which does not have the drawbacks of the starting sweetener, i.e. its poor solubility in water, its tendency to form dust or its strong hygroscopicity.

It does not involve granulating the aspartame as it is, but granulating the aspartame, by centrifugation, extrusion, spheronization or atomization techniques, with a binder consisting of maltodextrins, of dextrins, of gum arabic, of polyol, of polydextrose or of soluble starch.

However, it is necessary to introduce up to 40% of this granulation binder. Where maltodextrins are chosen as granulation binders, mixtures must contain from 15 to 25% by weight thereof.

Another drawback of these granulation binders is that they do not provide the active substance to be granulated with any nutritional plus-value.

It has therefore been recommended to produce granules of these active substances by incorporating dietary fiber into them.

The dietary fiber effects of several soluble starch derivatives have therefore been developed. These fiber effects are the result of both the combination of hydrolysis reactions and transglucosylation reactions which confer on said starch derivatives properties identical to those of dietary fiber (in Englyst and Cummings, American Journal of Clinical Nutrition, 1997, 45, pp. 423-431).

Thus, patent application JP No. 2000-37 169, discloses strong sweetener preparations (aspartame, saccharin, sucralose, neotame and derivatives thereof) that have a low energy value, that are not very viscous and that have physiological functions.

These novel low-calorie aspartame preparations are aspartame containing-granules with at least 30% by weight, or even at least 50% by weight, of dietary fiber, which are provided by indigestible dextrins.

The granulation procedure described in patent JP No. 2000-37 169 consist either in atomizing a mixed aqueous solution of an indigestible dextrin and of a strong sweetener or in creating a core of indigestible dextrins onto which said strong sweetener is sprayed.

However, in these two procedures, the indigestible dextrins must be introduced at high concentration. It is even recommended to introduce said indigestible dextrins in proportions reaching virtually the entire mixture.

It is in fact acknowledged that these strong sweeteners are active substances that are effective at low dose, given their sweetening power being up to 130 to 8000 times greater than that of sucrose.

These indigestible dextrins are therefore used as a carrier for active substances, and not as granulation binders. Consequently, they are only intended for granulation of active substances that are effective in very small amounts.

Patent application US 2002/0146.487 describes the coating of soybean proteins with a thin layer of indigestible carbohydrates, followed by a granulation step with lecithin.

However, the aim of this method is the production of readily dispersible soybean protein granules.

As a matter of fact, Soybean proteins already have excellent granulation capacities (cf. tofu, which is an agglomerated soybean protein).

The coating method is carried out in such a way as to prevent penetration of the carbohydrates into the protein agglomerate. The lecithin is chosen for its surfactant properties used conventionally for promoting protein dispersibility.

None of these two components is used in the patent application as a granulation binder, quite the contrary.

In view of the foregoing, it appears that there is no simple granulation method using a granulation binder that to provide a solution to the technological constraints of preparing granules of active substances in terms of mechanical stability (flow capacity, friability, rapid dissolution in water, compressibility) and to confer, on the resulting granules, additional nutritional properties (for example dietary fiber effects), without necessarily using large amounts of said granulation binder.

To the applicant company's credit, it has succeeded in reconciling these objectives, that are difficult to reconcile, by imaging and developing, at the expense of considerable research, a simple method for preparing granules of active substances containing dietary fiber.

SUMMARY OF THE INVENTION

The method for preparing granules of active substances containing dietary fiber in accordance with the invention consists in granulating a mixture of said active substances and branched maltodextrins having between 15 and 35% of 1-6 glucoside linkages, a reducing sugar content of less than 20%, a polymolecularity index of less than 5 and a number-average molecular mass Mn at most equal to 4500 g/mol, said branched maltodextrins content being of between 3 and 13% by weight of the mixture to be granulated.

These branched maltodextrins are naturally indigestible, which results in the reduction of their calorific value by preventing their assimilation in the small intestine. They are a source of indigestible dietary fiber.

By way of indication, their insoluble fiber content is generally more than 50% on a solids basis, which value is determined according to the AOAC method No. 985-29 (1986).

DETAILED DESCRIPTION OF THE INVENTION

Moreover, the low content of molecules with a low degree of polymerization, of said branched maltodextrins, also contributes to the reduced caloricity thereof.

Their high content of 1-6 glucoside linkages results in a decrease in their cariogenic capacity thanks to their reduced assimilation by the microorganisms leaving in the oral cavity.

This high level of 1-6 linkages also confers on them entirely specific prebiotic properties: it has in fact become apparent that the bacteria of the cecum and of the colon in humans and animals, such as the butyrogenic, lactic acid or propionic acid bacteria, metabolize highly branched compounds.

Furthermore, these branched maltodextrins promote the development of beneficial bifidogenic bacteria to the detriment of undesirable bacteria. This results in properties that are entirely beneficial to human health.

The applicant company has found that the incorporation of said branched maltodextrins into a mixture with active substances makes it possible to prepare granules of said active substances that have both excellent mechanical properties and physical properties, and also are a supply of indigestible fiber in applications to which conventional granulation binders could not aspire.

All the branched maltodextrins described in patent application EP 1 006 128 are suitable for preparing the granules of active substances according to the invention.

According to a preferred variant, said branched maltodextrins have a reducing sugar content of between 2 and 5% and a number-average molecular mass of between 2000 and 3000 g/mol.

According to another advantageous variant, all or some of these branched maltodextrins are hydrogenated.

For implementing the method for preparing the granules of active substances containing dietary fiber in accordance with the invention, it is chosen to incorporate from 3 to 13% of branched maltodextrins into the mixture to be granulated.

The applicant company has thus overcome a first technical prejudice, by choosing to use these branched maltodextrins in proportions that are conventional for a granulation binder, since it is established in the state of the art that granules containing dietary fiber means granules containing a large proportion of said fiber, to the detriment of the active substance to be granulated.

The applicant company has therefore established that the granulation binding capacity of its branched maltodextrins is observed for contents of between 3 and 13% by weight of the final mixture, preferably at a content of 5% by weight.

Moreover, as is known by specialists in the technical field of powder granulation, it is essential for the granulation binder to have an excellent capacity for dispersion in solution and a viscosity suited to the technical constraints of the materials used.

The applicant company has therefore overcome another technical prejudice relating to the use of branched maltodextrins as granulation binders, since, as will be exemplified hereinafter, a relative classification of the viscosities of soluble fibers available on the market indicates that the branched maltodextrins used are among the most viscous solutions of their category.

Surprisingly and unexpectedly, it has been noted that this viscosity does not in any way impair the formulation of the active substances, whatever the granulation method chosen.

In a first preferential embodiment of the method in accordance with the invention, the active substances to be granulated are chosen from the group consisting of starches and starch derivatives.

In a first variant, the starch derivatives are chosen from the group consisting of dextrins, indigestible dextrins, maltodextrins and branched maltodextrins.

The applicant company has in fact noted that, surprisingly and unexpectedly, the branched maltodextrins used as granulation binders advantageously strengthen the cohesion of the granules consisting of fillers that are themselves conventionally chosen as granulation binders.

As an illustration of this excellent ability to act as granulation binders of these particular fillers, the applicant company has succeeded in stabilizing the rheological behavior of powders of branched maltodextrins themselves, as will be exemplified hereinafter.

In a second variant, the starch derivatives are hydrogenated starch hydrolysates or conversion products of the hydrogenated starch hydrolysates, more particularly polyols, even more particularly polyols chosen from the group consisting of sorbitol, mannitol, xylitol and maltitol.

As an illustration of the ability of the branched maltodextrins to act as granulation binders for polyols, trials were undertaken by choosing two polyols that are particularly difficult to granulate, i.e. xylitol and mannitol, as will be exemplified hereinafter.

In a second preferential embodiment of the method in accordance with the invention, the active substances to be granulated are chosen from the group consisting of sugars, strong sweeteners, enzymes, vitamins and pharmaceutical active principles.

The applicant company chose to granulate the active substances using preferentially wet granulation techniques.

A first preferential method of granulation in accordance with the invention therefore consists in:

preparing a mixture of powdered active substances with branched maltodextrins that are also powdered, such that said branched maltodextrins content is of between 3 and 13%, preferably approximately 5%, by dry weight relative to the total solids content of the mixture, introducing water in a proportion of 5 to 20%, preferably in a proportion of 10%, by weight of the mixture thus prepared, so as to obtain a homogeneous mixture of wet powders, mechanically agitating the homogeneous mixture of wet powders thus obtained, in a mixer-granulator equipped with a sizing screen, recovering and drying the granules as they exit said screen.

The first step of this first method of granulation therefore consists in mixing the active substance to be granulated with from 3 to 13%, preferably of the order of 5%, by dry weight, of branched maltodextrins.

This operation is carried out by any means known to those skilled in the art. It may be chosen to mix the two components of the mixture in a planetary mixer of the Kenwood type.

The second step consists in preparing a homogeneous mixture of wet powders. This operation is carried out by introducing water, in a proportion of 5 to 20%, preferably in a proportion of 10%, by weight of the mixture.

The third step consists in granulating this homogeneous mixture of wet powders in a mixer-granulator equipped with a sizing screen. It may be chosen to carry this step out in a wet granulator of the Erweka FGS type.

In the final step of this method, the granules obtained are then dried and then sized on said sizing screen.

A second preferential method of granulation in accordance with the invention consists in:

preparing a solution of the branched maltodextrins at a solids content of between 10 and 50%, preferably at a solids content of approximately 25%, spraying the solution of branched maltodextrins thus obtained onto the powder of active substances, in a dryer-granulator, the branched maltodextrins content is of between 3 and 13%, preferably approximately 5%, by dry weight, of the total solids content of the mixture, recovering and drying the granules thus obtained.

The first step of this second method of granulation therefore consists in first of all preparing a solution of branched maltodextrins at a solids content of between 10 and 50%, preferably at a solids content of 25%.

The natural properties of rapid dissolution of the branched maltodextrins, greater than those of the standard equivalent maltodextrins, promote their solubilization at such a solids content.

The second step consists in spraying the resulting solution of branched maltodextrins onto the powder of active substances, the branched maltodextrins content is of between 3 and 13%, preferably 5%, by dry weight of the total solids content of the mixture. This procedure can advantageously be carried out in a dryer-granulator with a fluidized airbed of the Strea-1 type from Aeromatic, equipped with an injecting nozzle.

Despite the relative dynamic viscosity of the resulting maltodextrin solution, the applicant company did not notice any unfortunate problems:

of pumping of the solution of this granulation binder, of spraying at the outlet of the nozzles for injecting the liquid into the mass of particles of active substances moving in the granulator-mixer, of heterogeneity of the produced mixture, of disparity in the distribution of the droplets of the projected granulation binder.

The third step of this method consists, finally, in recovering and drying the resulting granules, by any means known to those skilled in the art.

This ability of the branched maltodextrins having between 15 and 35% of 1-6 glucoside linkages, a reducing sugar content of less than 20%, a polymolecularity index of less than 5 and a number-average molecular mass Mn at most equal to 4500 g/mol to readily granulate various active substances leads quite naturally to their use as granulation binders for preparing granules of active substances.

Other characteristics and advantages of the present invention will emerge clearly on reading the examples given hereinafter, which illustrate the invention without however limiting it.

Example 1

The relative viscosity of solutions of soluble fibers available on the market, that are capable of providing, as granulation binder, the granules of active substances with a nutritional component was determined in the following way.

The viscosity of these various products was measured by means of an Ares strain-controlled rotary rheometer (Rheometric Scientific) equipped with geometry of the cone-plate type. A shear gradient is applied to the product and the constraint (rotation couple) necessary for the shear is measured. The viscosity measurements (Eta) are expressed, in Pa·s, by the ratio between the constraint and the shear gradient. The measuring system is thermostatted and the temperature is maintained at +/−0.1° C.

Solutions containing a solids content of 25% of each of the commercial fibers are prepared, and the viscosity of said solutions is measured at a temperature of 20° C.

Table I below gives the relative viscosity of the branched maltodextrins chosen as granulation binders according to the invention, with regard to polydextrose, indigestible dextrins, fructo-oligosaccharides and galacto-oligosaccharides that are commercially available.

The viscosity index was set at 1 for the branched maltodextrins having a reducing sugar content of between 2 and 5% and a number-average molecular mass of between 2000 and 3000 g/mol used in the invention.

TABLE I

Relative classification of the viscosities of the soluble fibers of the market

| Name of the soluble fiber | Producer | Molecule type | Viscosity index |
|---|---|---|---|
| Litesse II | Cultor | Polydextrose | 0.6 |
| Pine fiber | Matsutani | Indigestible dextrin | 0.4 |
| Litesse I | Cultor | Polydextrose | 0.3 |
| Litesse III | Cultor | Polydextrose | 0.2 |
| Actilight 950 P | Beghin Meiji | Fructo-oligosaccharide | 0.2 |

TABLE I-continued

Relative classification of the viscosities of the soluble fibers of the market

| Name of the soluble fiber | Producer | Molecule type | Viscosity index |
|---|---|---|---|
| Cup Oligo P | Nisshin Seito | Galacto-oligosaccharide | 0.2 |
| Raftilose P95 | Orafti | Fructo-oligosaccharide | 0.2 |

It clearly appears that the branched maltodextrins used here have the highest viscosity index of their category, which means that they would not naturally be intended for use as granulation binders.

Example 2

In order to illustrate the ability of the branched maltodextrins to be able to act as granulation binders, said branched maltodextrins described in example 1 are granulated on themselves.

This ability of the branched maltodextrins to act as a granulation binder should improve their physical and mechanical properties, or even erase the deficiencies of the initial branched maltodextrin powder, in particular in terms of dust production.

A solution of branched maltodextrins with a 25% solids content (25 g of branched maltodextrins with 75 g of water) is prepared.

475 g of a branched maltodextrin powder having a mean particle size of 77 μm are placed in the bowl of the Aeromatic Strea-1 fluidized airbed dryer-granulator equipped with an injecting nozzle.

By means of air pulsed at the base of the bowl, the powder is suspended at a temperature of 60° C. The solution of branched maltodextrins is then sprayed at a flow rate of 4 ml/min and a pressure of 1 bar.

The granules recovered after 25 to 30 min of elapsed time are recovered and dried in the granulator for 30 minutes at 60° C. The granules are then sized on a sieve having a 1250 μm mesh size.

The particle size, the flow capacity, the aerated density and the compressibility of the resulting granules are then measured. A dust test is also carried out in order to determine the cohesion of the granules.

The size of the granules is measured on a Coulter® LS laser particle sizer, and is expressed by the arithmetic mean of the sizes of the particles (μm) obtained.

The flow of the granules is determined by means of a "funnel" test according to the pharmaceutical technical method 2.9.16 of the European Pharmacopeia, 3rd edition, and which consists in measuring the flow rate, expressed in seconds, of 100 g of granules deposited into a funnel whose dimensions are precisely given in this method.

The aerated density is, for its part, measured by means of a graduated cylinder test, which consists in using a 250 ml cylinder graduated every 2 ml. 100 g of granules weighed out with a precision of 0.5% are introduced without tapping into the dry cylinder. The apparent untapped volume Vo, estimated to within 1 ml, is then read.

The aerated density measured here corresponds to the ratio of the weight of granules (here 100 g) to the volume measured with the cylinder (Vo).

The compressibility measurement consists in determining the strength, expressed in Newtons, which corresponds to the resistance to the crushing of tablets, measured on a Schleuniger 2E durometer.

These tablets, produced on a Frogerais/Sviac alternating press equipped with concave punches 13 mm in diameter, from a mixture of 99.5% of granules in accordance with the invention and of 0.5% of magnesium stearate, are cylindrical in shape with convex faces (radius of curvature 13 mm), having a diameter of 13 mm, a thickness of 6 mm and a weight equal to 0.771 g, i.e. having a volume of 0.571 cm$^3$ and an apparent density of 1.35 g/cm$^3$.

Finally, the dust test consists in measuring the ability of a granule to release fine particles into a calibrated stream of air. For this measurement, a Heubach-Dustmeter device assembled in its type II configuration is used. 100 g of granules are introduced into the device, and subjected to a stream of air at a flow rate of 8 l/min for 5 min, at a temperature of 20° C.

The fine particles drifted by this stream of air are collected on a filter paper which is then weighed. The dust test consists in determining the weight of fine particles accumulated on the surface of the filter.

Table II below gives the results obtained on the granules of branched maltodextrins in accordance with the invention (granules A), in comparison with the initial powder of branched maltodextrins. Given as a control, are the results of the analyses carried out on the granules (granules B) obtained by taking, as granulation binder, a particular maltodextrin, sold by the applicant company under the brand name Lycatab® DSH as wet granulation excipient, instead of the branched maltodextrins, and carrying out the process in exactly the same way as for obtaining the granules A.

TABLE II

Results of analyses of the granules obtained

| | Starting branched maltodextrins | Granules A | Granules B |
|---|---|---|---|
| Particle size (μm) | 77 | 160 | 136.5 |
| Flow of powder(s) | 8 | 9 | 10 |
| Apparent density (g/ml) | 0.375 | 0.393 | 0.387 |
| Compressibility (N) | 250 | 190 | 195 |
| Dust test (g) | 0.0925 | 0.0221 | 0.0325 |

Granulation of the branched maltodextrins on themselves makes it possible to notably reduce the dust generated by the handling of the initial branched maltodextrin powders, while at the same time making it possible to obtain granules for which the flow capacity, the density and the compressibility are in accordance with what can be expected of an effective granulation binder, since the values are equivalent to those obtained with Lycatab® DSH.

Example 3

Crystalline xylitol sold by the applicant company under the brand name Xylisorb® 300 (mean particle size of 175.8 μm) is granulated with the branched maltodextrins of example 1, under the same conditions as those described in example 2.

Table III below gives the results of the analyses carried out on the xylitol granules prepared with the branched maltodextrins as granulation binders (granules C), in comparison with the starting xylitol powder.

Given as a control, are the results of the analyses carried out on granules obtained by also taking Lycatab® DSH as wet granulation binder, instead of the branched maltodextrins (granules D).

TABLE III

Results of analyses of the granules obtained

|  | Starting Xylisorb ® 300 | Granules C | Granules D |
|---|---|---|---|
| Particle size (μm) | 175.8 | 229 | 256 |
| Flow of powder(s) | infinite | 11 | 13 |
| Apparent density (g/ml) | 0.583 | 0.578 | 0.521 |
| Compressibility (N) | ND* | 130 | 120 |
| Dust test (g) | 0 | 0.0014 | 0.0024 |

ND*: not detectable

The granulation of the xylitol using the branched maltodextrins as granulation binders, just like the granulation carried out with Lycatab® DSH, make it possible to confer on the xylitol flow properties that it absolutely does not possess. This granulation is, moreover, the only way to confer on xylitol a satisfactory compressibility.

It should, however, be noted that, in addition to their additional supply of dietary fiber, the branched maltodextrins used as granulation binders improve the flow of the xylitol granules and limit slightly more the formation of dust, compared with Lycatab® DSH taken as conventional granulation binder.

Example 4

Crystalline mannitol is granulated with the branched maltodextrins of example 1.

950 g of crystalline mannitol sold by the applicant company under the name Mannitol P60 (mean particle size of 60 μm) are mixed with 50 g of a branched maltodextrin powder in a planetary mixer of the Kenwood type at minimum speed for 5 minutes.

Water is added in a proportion of 10 parts of water per 100 parts of the mixture thus obtained, and mixing is continued for 10 minutes.

The granulation is then carried out on an Erweka FGS wet granulator equipped with a 1000 μm screen, according to the constructor's specifications.

The granules obtained are then dried in an Aeromatic Strea-1 laboratory fluidized airbed dryer at a temperature of 60° C. for 30 min. The granules are then sized on said 1000 μm sizing screen (granules E).

As a control, Mannitol P60 is granulated with 5% of Lycatab® DSH, as wet granulation excipient (granules F), under the same operating conditions.

The results of the comparative measurements of the granules obtained with these two granulation binders, in terms of powder density, of flow time and of compressibility, carried out under conditions identical to examples 2 and 3, are given in table IV below.

The particle size measurements are here carried out on a Fritsch Analysette 3 laboratory electromagnetic sieving device, and are expressed as mean particle diameter (size of 50% of total particles).

TABLE IV

Results of analyses of the granules obtained

|  | Starting Mannitol P60 | Granules E | Granules F |
|---|---|---|---|
| Particle size (μm) | 60 | 860 | 860 |
| Flow of powder(s) | infinite | 13 | 13 |
| Apparent density (g/ml) | 0.588 | 0.540 | 0.550 |
| Compressibility (N) | ND* | 80 | 80 |

The granulation of the crystalline mannitol with the branched maltodextrins as granulation binders makes it possible to obtain granules for which the flow capacity, the density and the compressibility are in accordance with what can be expected from an effective granulation binder, since the values are equivalent to those obtained with Lycatab® DSH. The intrinsic nature of the branched maltodextrins as dietary fiber can thus be fully taken advantage of, in addition to their properties as granulation binders.

The invention claimed is:

1. A method for preparing granules of active substances containing dietary fiber, consisting of:
    granulating a mixture of active substances and branched maltodextrins having between 15 and 35% of 1-6 glucoside linkages, a reducing sugar content of between 2 and 5%, a polymolecularity index of less than 5 and a number-average molecular mass Mn of between 2000 and 3000 g/mol said branched maltodextrins content is between 3 and 13% by weight of the mixture to be granulated,
    wherein the active substances are selected from the group consisting of starches, starch derivatives, sugars, strong sweeteners, enzymes, vitamins, and pharmaceutical active principles, and the active substances do not include soybean proteins.

2. The method as claimed in claim 1, wherein the active substances are selected from the group consisting of starches and starch derivatives.

3. The method as claimed in claim 2, wherein the starch derivatives are selected from the group consisting of dextrins, indigestible dextrins, maltodextrins and branched maltodextrins.

4. The method as claimed in claim 2, wherein the starch derivatives are hydrogenated starch hydrolysates or conversion products of the hydrogenated starch hydrolysates.

5. The method as claimed in claim 4, wherein the starch derivatives are polyols.

6. The method as claimed in claim 5, wherein the polyols are selected from the group consisting of sorbitol, mannitol, xylitol and maltitol.

7. The method as claimed in claim 1, wherein said active substances are selected from the group consisting of sugars, strong sweeteners, enzymes, vitamins and pharmaceutical active principles.

8. The method as claimed in claim 1, wherein said granulating is performed by:
    preparing a mixture of powdered active substances with powdered branch maltodextrins such that said branched maltodextrins content is of between 3 and 13%, by dry weight relative to the total solids content of the mixture,
    introducing water in a proportion of 5 to 20%, by weight of the resulting mixture, so as to obtain a homogeneous mixture of wet powders,
    mechanically agitating the resulting homogeneous mixture of wet powders, in a mixer-granulator equipped with a sizing screen, and
    recovering and drying the granules as they exit said screen.

9. The method as claimed in claim 8, wherein said maltodextrins content is of approximately 5% by dry weight relative to the total solids content of the mixture.

10. The method as claimed in claim 8, wherein the water introduced is in a proportion of 10% by weight of the resulting mixture, so as to obtain a homogeneous mixture of wet powders.

11. The method as claimed in claim 1, wherein said granulating is performed by:
preparing a solution of branched maltodextrins at a solids content of between 10 and 50%,
spraying the resulting solution of branched maltodextrins onto the powder of active substances, in a dryer-granulator, the branched maltodextrins content is of between 3 and 13%, by dry weight of the total solids content of the mixture, and
recovering and drying the resulting granules.

12. The method as claimed in claim 11, wherein the solution of branched maltodextrins to be prepared has a solids content of approximately 25%, by dry weight of the total solids content of the mixture.

13. The method as claimed in claim 11, wherein the solution of branched maltodextrins to be sprayed has a content of approximately 5%, by dry weight of the total solids content of the mixture.

14. The method as claimed in claim 1, wherein the maltodextrins having between 15 and 35% of 1-6 glucoside linkages, a reducing sugar content of less than 20%, a polymolecularity index of less than 5 and a number-average molecular mass Mn at most equal to 4500 g/mol are used as a granulation binder for active substances.

15. A method for preparing granules of active substances containing dietary fiber, comprising:
granulating a powdered mixture of active substances selected from the group consisting of starches, starch derivatives, sugars, strong sweeteners, enzymes, vitamins, and pharmaceutical active principles, and branched maltodextrins having between 15 and 35% of 1-6 glucoside linkages, a reducing sugar content of between 2 and 5%, a polymolecularity index of less than 5 and a number-average molecular mass Mn of between 2000 and 3000 g/mol, said branched maltodextrins content is between 3 and 13% by weight of the mixture to be granulated,
wherein the active substances do not include soybean proteins.

16. The method as claimed in claim 15, wherein the active substances are selected from the group consisting of starches and starch derivatives.

17. The method as claimed in claim 15, wherein the starch derivatives are selected from the group consisting of dextrins, indigestible dextrins, maltodextrins and branched maltodextrins.

18. The method as claimed in claim 15, wherein the starch derivatives are hydrogenated starch hydrolysates or conversion products of the hydrogenated starch hydrolysates.

19. The method as claimed in claim 15, wherein the starch derivatives are polyols.

20. The method as claimed in claim 15, wherein said granulating comprises the steps of:
preparing a mixture of powdered active substances with powdered branch maltodextrins so that said branched maltodextrins content is between 3 and 13%, by dry weight relative to the total solids content of the mixture,
introducing water in a proportion of 5 to 20%, by weight of the resulting mixture, so as to obtain a homogeneous mixture of wet powders,
mechanically agitating the resulting homogeneous mixture of wet powders, in a mixer-granulator equipped with a sizing screen, and
recovering and drying the granules as they exit said screen.

21. A method for preparing granules of active substances containing dietary fiber, comprising:
granulating a mixture of active substances selected from the group consisting of starches, starch derivatives, sugars, strong sweeteners, enzymes, vitamins, and pharmaceutical active principles, with a granulation binder consisting of branched maltodextrins having between 15 and 35% of 1-6 glucoside linkages, a reducing sugar content of between 2 and 5%, a polymolecularity index of less than 5 and a number-average molecular mass Mn of between 2000 and 3000 g/mol, said branched maltodextrins content is between 3 and 13% by weight of the mixture to be granulated,
wherein the active substances does not include soybean proteins.

* * * * *